US012806294B2

(12) United States Patent
Remmerswaal

(10) Patent No.: US 12,806,294 B2
(45) Date of Patent: Nov. 24, 2026

(54) ECHOGENIC IMAGE ENHANCING COMPOSITIONS, PREPARATION AND USE THEREOF

(71) Applicant: Giskit B.V., Rotterdam (NL)

(72) Inventor: Johannes Franciscus Marinus Remmerswaal, Rotterdam (NL)

(73) Assignee: Giskit B.V., Rotterdam (NL)

( * ) Notice: Subject to any disclaimer, the term of this patent is extended or adjusted under 35 U.S.C. 154(b) by 254 days.

(21) Appl. No.: 16/626,372

(22) PCT Filed: Jun. 27, 2018

(86) PCT No.: PCT/NL2018/050416
§ 371 (c)(1),
(2) Date: Dec. 24, 2019

(87) PCT Pub. No.: WO2019/004828
PCT Pub. Date: Jan. 3, 2019

(65) Prior Publication Data
US 2021/0145986 A1 May 20, 2021

(30) Foreign Application Priority Data
Jun. 30, 2017 (NL) ...................................... 2019159

(51) Int. Cl.
*A61B 8/00* (2006.01)
*A61K 9/12* (2006.01)
*A61K 47/44* (2017.01)
*A61K 49/22* (2006.01)
*A61M 5/00* (2006.01)
*A61M 5/19* (2006.01)

(52) U.S. Cl.
CPC ............ *A61K 49/223* (2013.01); *A61B 8/481* (2013.01); *A61K 9/12* (2013.01); *A61K 47/44* (2013.01); *A61M 5/007* (2013.01); *A61M 5/19* (2013.01); *A61M 2210/1425* (2013.01)

(58) Field of Classification Search
CPC ........ A61K 49/223; A61K 9/12; A61K 47/44; A61B 8/481; A61M 5/007; A61M 5/19; A61M 2210/1425
See application file for complete search history.

(56) References Cited

U.S. PATENT DOCUMENTS

2001/0024638 A1* 9/2001 Schneider ............ A61K 49/223 424/9.51
2003/0185759 A1 10/2003 Schneider et al.

FOREIGN PATENT DOCUMENTS

WO 2011/046437 A1 4/2011

OTHER PUBLICATIONS

Dreyer et al., N. Engl. J. Med 376;21 (2017) (Year: 2017).*
Rajesh et al., Int'l J. Women's Health 2017:9 23-32. (Year: 2017).*
Mukund et al., Cardiovasc Intervent Radiol (2017) 40:1010-1016. (Year: 2017).*
Anonymous: "LIPIODOL (Ethiodized Oil), Injection", Mar. 1, 2014 (Mar. 1, 2014), XP055458137, Retrieved from the Internet: URL:https://www.accessdata.fda.gov/drugsatfda_docs/label/2014/009190S021lbl.pdf [retrieved on Mar. 9, 2018], whole document and in particular p. 1, first paragraph, "Description".
Shrestha L K et al: "Stabilization of nonaqueous foam with lamellar liquid crystal particles in diglycerol monolaurate/olive oil system", Journal of Colloid and Interface Science, Academic Press, Inc, US, vol. 328, No. 1, Dec. 1, 2008 (Dec. 1, 2008), pp. 172-179, XP025589363, ISSN: 0021-9797, DOI: 10.1016/J.JCIS.2008.08.051 [retrieved on Sep. 3, 2008] the whole document and in particular the abstract, sections "2.2. Method" and 3.
Binks, Bernard P et al: "Ultra-stable self-foaming oils", Food Research International, Elsevier, Amsterdam, NL, vol. 95, Mar. 1, 2017 (Mar. 1, 2017), pp. 28-37, XP029973978, ISSN: 0963-9969, DOI: 10.1016/J.FOODRES.2017.02.020, the whole document and in particular the abstract and section "3. Results and discussion".

* cited by examiner

*Primary Examiner* — Robert S Cabral
(74) *Attorney, Agent, or Firm* — Ipsilon USA - NLO

(57) ABSTRACT

The invention pertains to an echolucent image enhancing hydrophobic, water-immiscible composition, wherein the composition turns echogenic when foamed with air or gas bubbles formed from mechanically inserting (i) air or gas; or (ii) aqueous solution with air or gas into the hydrophobic, water-immiscible composition. The invention also pertains to a foamed echogenic image enhancing hydrophobic, water-immiscible composition and optionally comprising aqueous solution forming a single-phase, said composition comprising air or gas bubbles retained in the composition, and wherein the volume ratio of aqueous solution:hydrophobic, water-immiscible composition is preferably in the range of between 0:100 (i.e. no aqueous solution) and 75:25, preferably between 0:100 and 60:40.

15 Claims, No Drawings

ECHOGENIC IMAGE ENHANCING COMPOSITIONS, PREPARATION AND USE THEREOF

FIELD OF THE INVENTION

The present invention relates to the field of echography or sonohysterography, particularly concerning the evaluation of fallopian tubal patency in infertility investigations, and controlling of fallopian tube sterilization.

BACKGROUND OF THE INVENTION

Medical diagnostic imaging is used for the examination of body cavities. Prior to the imaging procedure a fluid is instilled into the body cavity which has two basic functions: to open the cavity from a possible collapsed state (distension) and to enhance the contrast of the image of the body cavity. The instillation of fluid is also used to examine if there is an open fluid communication in a body vessel or to display if the vessel is obstructed.

Two completely different techniques are commonly used to obtain medical diagnostic images: radiology and echography. These techniques use different physical detection means and different instrumentation, other contrast agents and human skills to obtain medical diagnostic images.

Radiology or X-ray imaging uses Rontgen radiation or X-rays. The radiation penetrates through living tissues, which are completely transparent for X-rays, with the exception of bones. The contrast can only be obtained by adding radiopaque (i.e. non-transparent for X-rays) substances to an instilled fluid. Examples of suitable radiopaque contrast agents are particles containing heavy atoms or dissolved Iodide to obtain the required ‘very dense’ radiopaque fluid. X-rays can damage living tissue, so great care needs to be undertaken to keep the dose of X-rays as low as possible. For radiological diagnostics both water-based hydrophilic and oil-based hydrophobic fluids are used to dissolve or carry the radiopaque contrast agents, where the fluids do not contribute to the contrast. Since these radiological contrast agents can be harmful if spilled into the body, also care must be undertaken to confine the agent to the body part under investigation and the removal or breakdown in the body after the investigation should not be harmful.

In radiology essential very dense fluids containing radiopaque substances must be used, to generate the contrast versus the living tissue which is transparent, any air or gas bubbles will vitiate the activity of the contrast fluid by rendering it less dense for radiological purposes, destroy the contrast and must be avoided. The dense fluids used must be confined and removal or breakdown pathways, which insure that the health of the patient is not impaired, must be available. Both oil based hydrophobic and water based hydrophilic compositions are commonly used in radiology to dissolve the radiopaque substances. Lipiodol (labelled Ethiodol in the USA), also known as ethiodized oil, is a good example of such radiopaque composition used in hysterosalpinography (X-rays). Current health insights are that X-rays are not desired in subfertility investigations.

On the other end, echography or sonohysterography is a different technique to obtain medical diagnostic images, making use of ultrasound waves. This method produces excellent images and the ultrasound waves are absolutely harmless for living tissues. For the ultrasound waves the living tissue is not transparent but visible. To get better details about a cavity under investigation the fluid instilled must be non-echogenic and transparent for the ultrasound waves to obtain a detailed image of the walls and surrounding of the cavity. Conventionally, only water or watery fluids have been used for distension and contrast imaging with ultrasound.

In intervention cardiology or radiology, kidneys, liver, intestines, the water-based fluids are sometimes combined with the generation of bubbles, to further increase contrast in the veins. Use of so-called microbubbles is disclosed in U.S. Pat. No. 4,681,119 where extremely short-living bubbles are described. In order not to cause any hazards in the bloodstream, these bubbles should be small (typically less than 10 microns) and uniform in size.

EP 1.793.860 provides a solution to overcome the inconveniences and discomfort caused by leakage of aqueous solutions while imaging. Thereto, it discloses a hydrophilic water gel composition having a viscosity of between 2000 and 4000 mPa·sec, containing cellulose or cellulose derivative. The composition may be used for the imaging of any body cavity. The commercially available ExEm® falls within the scope of EP 1.793.860. The gel described therein is stable and does not contain any particles or microbubbles which otherwise would be perceived to result in artefacts.

It goes without saying that the skilled person in the field of sterilization and fertility investigations is searching for particle-free, embryotoxic-free but cost-effective solutions for imaging of fallopian tubes which are easy-to-handle, enable high quality images without jeopardising the health of the patient and without loss of echogenicity during imaging. Adhesion is to be prevented at all cost. With these aims in mind, WO2011/046437 discloses a foamed echogenic image enhancing hydrophilic composition based on the hydrophilic aqueous gel of ExEm®. By pumping water into the echolucent water-based ExEm® the viscosity of the gel is lowered and air bubbles are introduced yet remain trapped in the aqueous matrix, thus forming a stable foam. The instilled watery foam filling of the vessel acts as a contrast agent and will be clearly visible on the ultrasound image. This procedure is especially useful if the openness of a vessel such as the fallopian tubes is the object of the investigation. Excellent reports have been received that filling of the fallopian tubes with hydrophilic foamed ExEm® is much easier to practitioner (gynaecologist) and patient (not necessitating any need for excessive force), and the air bubbles enhanced visualization while imaging. The composition is sufficiently viscous to provide a stable distribution of gas bubbles during examination, while at the same time its reduced viscosity and permits easy insertion into the fallopian tubes. The composition can hold the air pockets for a time sufficiently long to perform imaging without loss of echogenicity. In the state of the art of the echography or sonohysterography only watery fluids or compositions of water and hydrophilic fluids are used.

It remains to be emphasized that the contrast agents suitable for ultrasound and radiology serve to create contrast in completely different physical ways and completely different physical detection means, and above all by different physicians (radiologist vs. gynaecologist), as ultrasound and X-rays used are physical different, the one consisting of sound waves above the audible spectrum to the ear, and the other of high-frequency electromagnetic radiation (X-rays); consequently the agents have been designed to satisfy completely different and unrelated physical properties.

There remains a need for alternative solutions in sonography or HyCoSy in the art.

SUMMARY OF THE INVENTION

The inventors have found that in the application of echography or sonohysterography with ultrasound excellent medical diagnostic images could be obtained using hydrophobic oils and on hydrophobic fluids based compositions. It was found that similar goals, both for the use as echolucent distension as well as use as hyperechoic foam can be achieved in echography, using hydrophobic oils and on hydrophobic fluids based compositions. In the above mentioned state of the art no indication can be found, that a person skilled in the art of X-ray imaging will consider and apply bubbles in hysterosalpinography (HSG), nor an indication that a hydrophobic fluid which is intended to carry the radiopaque substance for HSG, should be considered by a person skilled in the art of echography, to be useful for a composition with bubbles as contrast agent in ultrasound echography.

A number of inventive hydrophobic compositions for echogenic use have been investigated. The investigations showed that using a foamed particle-free embryotoxic-free composition comprising a continuous hydrophobic, water-immiscible matrix, wherein hyperechoic air (bubbles) is mixed, all or not together with addition of very small quantities of water or aqueous solution (e.g. saline or purified water) into the hydrophobic water-immiscible matrix, the foamed gas remains dispersed in the hydrophobic water-immiscible composition for a time long enough for the medical practitioner to fill the fallopian tubes and carry out (medical) imaging. For sake of analogy, the echogenic composition with water/air bubbles entrained in the hydrophobic, water-immiscible matrix will be referred to being 'foamed'. With "foamed" it is understood that the gas inserted into the hydrophobic, water-immiscible composition is maintained within the composition for at least 30 seconds, preferably at least 1 minute, more preferably at least 2 minutes, most preferably at least 5 minutes, after preparation.

The bubbles introduced mechanically will be maintained in the hydrophobic, water-immiscible matrix rendering it a 'milky' or 'white' appearance. Although not considered detrimental to the invention, foam stability over time periods extending beyond 10 minutes are generally not preferred. Over the above time periods, the foam is stable, meaning that the hydrophobic composition retains its excellent echogenic properties over that time. In the context of the invention, the 'air bubbles' mean small air or gas particles or pockets entrained and dispersed in the hydrophobic, water-immiscible fluid, and as milky substance visible to the eye. Very advantageously, dilution results in reducing viscosities while foaming surprisingly increases the dynamic fluidity and hence the ease with which body cavities such as vessels can be filled easier. The patency test examination of the fallopian tubes for blockage, preventing pregnancy, either desired or undesired, is an application where these properties are important, as the fallopian tubes have a very small flow diameter, and are very sensitive to the filling with a contrast fluid.

The inventors have found that some hydrophobic oils, such as Lipiodol®, up to now only applied in the radiology for HSG with X-rays, could be used in echography or sonohysterography with ultrasound in fallopian tube openness or patency investigation, provided a foam is produced. The filling procedure of the fallopian tubes with the hydrophobic foam is easy and painless, and can be performed at low pressure, and above all produces excellent images with ultrasound. The use of these hydrophobic oils, albeit foamed, is much safer in subfertility investigations as the corresponding radiological procedure where the oil is pumped under considerable pressure as a dense fluid into the fallopian tubes, producing pain and distress in the patient, after which the patient is subjected to a dose of X-rays to produce a by radiology detectable image. Advantageously, the hydrophobic foam produces less rest fluid. These insights render it possible to turn hydrophobic oils originally applied only for hysterosalpingografie (HSG) in radiological procedures with X-rays, suitable for echography and sonohysterography, where the procedures are painless and much safer in subfertility investigations, produce less rest fluid, and use completely harmless ultrasound to produce medical diagnostic images of excellent quality.

In one embodiment the air or gas is inserted together with water or aqueous solution into the hydrophobic, water-immiscible composition. While the use of (sterile) gas or air alone suffices to retain a stable distribution of bubbles which remain trapped for the time scales needed for imaging, the water of aqueous solution (e.g. saline or purified water) was found to improve foaming. The water-immiscible composition and the optional aqueous phase may form a kinetically stable w/o emulsion with small air pockets entrapped, and wherein 'kinetically stable' refers to the stability times mentioned above, which are typically needed for the skilled practitioner to prepare and place the device, and perform (medical) imaging by ultrasound.

The hydrophobic, water-immiscible composition can be an ethiodized oil such as Lipiodol (Ethiodol), which is an ethiodized poppyseed oil. Recently, Lipiodol has attracted renewed attention as a therapeutic agent in the management of unexplained infertility, using a procedure called Lipiodol flushing. There has been a number of studies that suggest that flushing the oil media through the tubes gives a short-term rise in fecundity in patients with unexplained infertility. A systematic review has suggested a significant increase in fertility, especially in those women who have endometriosis when using Lipiodol flushing. This goes back a long way, in a Yale infertility Clinic study reported by Mackey et al. "Pregnancy following hysterosalpingography with oil and water soluble dye" Fertil. Steril. Vol. 22(8) (1971) pages 504-507. It was suggested that Ethiodol HSG may enhance fertility there, and reiterated by Rasmussen et al. "Therapeutic effect of hysterosalpingography: oil-versus water-soluble contrast media—a randomized prospective study" Radiology vol. 179(1) (1991) pages 75-78. It is however an insight of the inventors to use these oils suited for HSG as an echogenic composition suitable in sonohysterography with ultrasound. The use of Lipiodol as an echogenic image enhancing composition for assessing tubal patency in infertility investigations with ultrasound thus brings a number of additional advantages to the patient. Without wishing to be tied down to any theory, the oil is believed it could have an advantageous fertility benefit, which may lead to the conclusion that it has an impact on endometriosis.

In a preferred embodiment the water-immiscible composition comprises tocopherol equivalents, preferably at least alpha-tocopherol. It is believed that tocopherol may stimulate fertility, and hence it is preferred to use hydrophobic compositions that are known to be naturally high in alpha-tocopherol, such as safflower oil, canola oil, wheat germ, rapeseed oil, cottonseed oil and sunflower oil. The hydrophobic, water-immiscible composition thus preferably comprises safflower oil, canola oil, wheat germ, rapeseed oil, cottonseed oil and/or sunflower oil.

The rest fluid of the hydrophobic, water-immiscible foamed composition can conveniently at least in part be removed after sonohysterography with ultrasound by applying a slight underpressure, which does not cause pain or distress to the patient.

DESCRIPTION OF EMBODIMENTS

In one aspect, the present invention relates to a foamed, echogenic image enhancing composition, suitable for (medical) imaging of the fallopian tubes, said composition comprising a continuous hydrophobic, water-immiscible matrix. In a preferred aspect, the invention pertains to a foamed echogenic medical image enhancing hydrophobic, water-immiscible composition, optionally comprising water, preferably forming a water-in-oil (w/o) emulsion, comprising air or gas bubbles retained in the hydrophobic water-immiscible composition, and wherein the volume ratio of water:hydrophobic, water-immiscible composition is in the range between 0:100 (i.e. no aqueous solution) and 75:25, preferably between 0:100 and 60:40, preferably between 1:99 and 50:50, more preferably between 5:95 and 40:60, most preferably between 10:90 and 25:75.

Worded differently, in a first aspect the invention pertains to a foamed echogenic medical image enhancing hydrophobic, water-immiscible composition, suitable for echography or sonohysterography, said composition comprising air or gas bubbles retained in the hydrophobic water-immiscible composition. In a further aspect, the invention relates to a foamed echogenic medical image enhancing hydrophobic, water-immiscible composition, suitable for echography or sonohysterography, said composition comprising water and further comprising air or gas bubbles retained in the hydrophobic water-immiscible composition, and wherein the volume ratio of water:hydrophobic, water-immiscible composition is in the range between 1:99 and 75:25, preferably between 1:99 and 60:40.

Associated therewith, the invention also pertains to an echolucent image enhancing hydrophobic, water-immiscible, wherein the composition turns echogenic when foamed with air or gas bubbles formed by mechanically inserting, preferably pumping (sterile) air in a syringe—all or not together with water or aqueous solution—into the hydrophobic, water-immiscible composition.

The hydrophobic component preferably has a low viscosity, preferably less than 1500 mPa·sec, more preferably less than 1000 mPa·s, most preferably less than 750 mPa·s, particularly less than 500 mPa·s., even more preferably less than 250 mPa·s, as determined by standard viscosity determination methods, measured at room temperature and under atmospheric pressure. Unless mentioned otherwise, the viscosity numbers in the context of the invention are the dynamic viscosities determined using a Brookfield rotational viscometer, at room temperature (e.g. 25° C.).

The composition is preferably non-embryotoxic.

A hydrophobic, water-immiscible composition complies with the above constraints of being echolucent and preferably non-embryotoxic. The skilled person has no difficulties selecting an appropriate oil-based matrix from those oil-miscible contrasting fluids there are commercially available, preferably those already known being suited for X-ray or HSG. The hydrophobic composition can be a pharmaceutical oil or a naturally occurring oil, such as there are aricinoleic acid (12-hydroxy-9-cis-octadecenoic acid), lesquerolic acid, esters derived from aricinoleic acid and/or lesquerolic acid with glycerol: monoglycerides, diglycerides triglycerides (oil) or ethanol (ethyl esters), poppy seed oil, glycerol esters of poppy seed oil, ethyl esters of poppy seed oil, oils containing tocopherol, tocopheryl esters, tocotrienols, phytosterols, campesterol, stigmasterol, sitosterol, poppy seed oil, palm oil, rice bran oil, wheat germ, sunflower oil or almond oil, or mixtures thereof. As addressed above, it is preferred that the oil is high in tocopherol equivalents, particularly high in alpha-tocopherol, such as wheat germ and sunflower oil.

Most preferred are those oils having tocopherol equivalents.

After sonohysterography, the foam dissolves to the initial state. Even if the fallopian tubes are physical open, many other factors are needed for successful fertilisation. The tubes are covered with ciliated epithelia and peg cells which are very important and sensitive. The cells facilitate fertilisation by providing condition of tubular fluid, promotes capacitation of the sperm, and moving the zygote to the uterus. Mucus and/or slime forming by inflammatory and/or allergic reactions can completely vitiate the correct functioning of the (not blocked) tubes. The composition of the invention is believed to improve the condition of the fallopian tubes after the sonohysterography test, and thus bring a great advantage. The foam could also be used without sonohysterography as very easy means of administering such fallopian tubes condition improving starting fluid.

In one embodiment, the hydrophobic oil-miscible compositions are based on poppyseed oil, ethiodized oil or ethiodized poppyseed oil, LIPIODOL®, tetrafluorodibromoethane, and hexafluorodibromopropane. In one embodiment the oil is a triglyceride-containing oil, preferably castor oil. Triglycerides are further believed to add to increase in fertility.

'Echolucent' means that passage of ultrasonic waves are permitted through the composition without giving rise to echoes, the representative areas appearing black on the sonogram. The term 'echogenic' means that it gives rise to reflections (echoes) of ultrasound waves.

The (foamed) image enhancing composition of the invention preferably does not comprise any detectable amounts of cellulose and cellulose derivative(s) derivatives.

The viscosity of the foamed composition is preferably less than 1500 mPa·s, more preferably less than 1000 mPa·s, most preferably less than 750 mPa·s, particularly less than 500 mPa·s, most preferably less than 250 mPa·s. The actual viscosity may be readily set by the medical examiner (gynaecologist) when preparing the foam, depending on the application: The increased fluid dynamics are particularly preferred when examining the fallopian tubes after fallopian tube sterilization surgery. At lower viscosities, the risk of pressure build-up, pain and potential damage to the tubes is avoided. The lower viscosities may however necessitate catheters. It is preferred that the viscosity of the composition is more than 4 mPas, more preferably more than 5 mPas, even more preferably more than 10 mPas, particularly more than 15 mPas, most preferably more than 20 mPas. This way leakage of image enhancing composition is minimized, and foam stability is guaranteed. The composition may be used in connection with catheters known in the art. Excellent results are obtained with the sealing stopper and assembly disclosed in WO2007/030002, herein incorporated by reference.

The skilled person will understand that adjuvants, such as disinfectants or a local anaesthetic, may be present in the composition, for instance lidocaine and chlorohexidine. It may be preferred to use such anaesthetics when examining after intratubal placement. In other embodiments the use of local anaesthetics is not preferred or even avoided. Any further ingredients are preferably non-embryotoxic (i.e. anything which can adversely affect the growth or development of the embryo).

The non-foamed hydrophobic, water-immiscible composition should be echolucent and therefore not contain any detectable amounts of particulate material. Consequently, the foamed composition is free from any detectable amounts of (solid-state) particulate material too. The composition is distinct from those prior art medical imaging compositions comprising non-settling powdered agents suspended therein.

In order to optimize the stable formation of gas bubbles or pockets using water or aqueous solutions it is preferred to refrain from the use of surfactants.

In the context of the invention, the foamed composition may be characterized being a colloidal gas emulsion, with the gas representing the dispersed phase and the hydrophobic liquid the continuous phase. The structure of the foam is described by the density of the foam combined with the bubble diameter distribution. Foams are highly compressible media wherein the flow characteristic is not adequately described by the viscosity like in liquids. In such context, the term apparent viscosity is used and is a function of foam density and bubble diameter distribution. In order to achieve easier handling of the imaging composition in the fallopian tubes, it is preferred that the size of the bubbles is smaller than the passage diameter, whereby the fluidity is increased as the bubbles are able to deform in order to pass each other. If the ratio between the passage diameter and the bubble diameters is large the slip velocity is not only dependent on shear stress at the wall of the passage but also on the passage diameter, which causes the fluidity to increase. The inventors thus realized that rheological properties in particular the high deformability and high fluidity of a foam make it particularly suitable for establish filling of the fallopian tubes at low applied pressure.

The closed cell structure of a foam is produced from bubbles, after which a stable foam is obtained as a highly flexible, compressible and fluid body, which does not release bubbles as result of the viscoelastic forces. After use the foam will dissolve in a defoaming process, leaving only a small amount of liquid.

In the art, a foam is unmistakably different from microbubbles in echography or sonohysterography, in terms of size, size distribution and densities. Microbubbles used for contrast in the art typically have a volume-weighted median diameter (D50) below 10 micrometer, and narrow particle size distributions. In a foam, the air pockets have a volume-weighted average median particle size of greater than 50 microns, preferably up to 500 micron, more preferably up to 250 micron, most preferably up to 100 micron, for instance determined using optical microscopy. Also, the density of bubbles in a foam according to the invention is less than 1*10ˆ6 (<1,000,000) bubbles/ml, preferably less than 1*ˆ5 bubbles per ml, in contrast with the much larger densities of (smaller) microbubbles or 'microspheres' necessary in echography or sonohysterography.

In a preferred embodiment the hydrophobic composition with air bubbles entrapped forms an water-in-oil (w/o) emulsion with an aqueous component and air bubbles or air pockets dispersed in the hydrophobic continuous matrix for the time ranges mentioned above, meaning that the mixture with the aqueous phase and air bubbles or pockets dispersed or entrapped in the hydrophobic continuous matrix is kinetically stable for a time span of at least 30 seconds, preferably at least 1 minute, more preferably at least 2 minutes, more preferably at least 5 minutes, after mixing was stopped. The hydrophobic matrix thus preferably forms a single phase, to the eye.

The present invention also pertains to a method for preparing such a foamed composition by (i) providing an hydrophobic, water-immiscible composition, and (ii) inserting gas or air, optionally in combination with aqueous solution, into said composition (i.e. foaming), to produce a foamed composition with gas or air bubbles entrained or dispersed in the continuous hydrophobic, water-immiscible matrix, and having a viscosity within acceptable levels as defined herein.

The "insertion" can be realized by all means that result in foaming, typically mechanically, by pumping e.g. using a syringe.

Although there are no limitations regarding the ways to insert air bubbles into the hydrophobic, water-immiscible composition this may conveniently be achieved by (i) pumping (sterile) air or (ii) pumping (sterile) air and (demineralised or purified) water or saline salt solution, preferably using a syringe, both considered included in the term "aqueous solution", into the hydrophobic, water-immiscible composition.

Conveniently, foam may be realized by the practitioner or assistant in the presence of the patient immediately prior to (medical) imaging of the fallopian tubes, preferably by connecting a first syringe (cylinder/piston), containing a predetermined amount of the echolucent hydrophobic, water-immiscible composition, with a second syringe, filled with a predetermined amount of (a) (sterile) air or (b) aqueous solution and (sterile) air, and pumping the contents of the second syringe and the first syringe back and forth, thus mixing until a suitable foam in the hydrophobic, water-immiscible composition is formed, and an echogenic composition is thus yielded. The syringes may be connected using simple (medical) tubing, optionally with a mixing chamber in-between. The mixing chamber has an outlet for dispensing the foamed composition. The device may be used in combination with standard intrauterine catheters.

In one embodiment, use can be made of existing contrast delivery technology for in-office tubal patency evaluation with sonohysterography (or HyCoSy) as there are air bubble based infusers (e.g. ABBI Air Bubble Based Infuser (CooperSurgical)) with a dual chamber design with a first chamber of the hydrophobic composition and a second chamber with (i) air or (ii) saline and air (said second chamber preferably having an inlet for air or sterile aqueous solution and air), wherein the two cylinder/piston chambers are in fluid connection in a mixing zone for preparing the foam according to the invention, and an outlet for dispensing the foamed composition. The device may be used in combination with standard intrauterine catheters.

Medical imaging preferably concerns a patency test or a fallopian tube sterilization check.

The relative amounts of the hydrophobic, water-immiscible composition and the air or gas (all or not comprised in aqueous solution) are selected such that the end viscosity is within the desired range and sufficiently foaming is established. This may conveniently be assessed by the medical practitioner, and he may adjust the amount of (i) air or (ii) air and aqueous solution mixed with the hydrophobic, water-immiscible composition according to his or her needs. In those embodiments wherein the hydrophobic matrix is foamed using aqueous solution and air (in order to enhance foaming), a syringe containing the (maximum allowable amount of) aqueous solution, said syringe having a calibrated scale, preferably even in combination with an instruction manual that helps to convert the numbers in terms of viscosities, may be of help.

As a guide, the volume ratio aqueous solution: hydrophobic, water-immiscible composition in the mixing step (i.e. foaming the hydrophobic, water-immiscible composition) is preferably between 0:100 (i.e. no aqueous solution) and 75:25, preferably between 0:100 and 60:40, preferably between 1:99 and 50:50, more preferably between 5:95 and 40:60, most preferably between 10:90 and 25:75. The hydrophobic continuous matrix preferably is the predominant component. The amount of aqueous solution should be controlled in order to maintain the hydrophobic, water-immiscible composition forming a continuous matrix in which the gas or air bubbles are dispersed. It was found that within these ranges a kinetically stable mixture of oil and water with bubbles entrapped in the oil matrix was obtained for a period over at least 10 minutes.

The present invention also pertains to a kit of parts comprising (i) an echolucent image enhancing hydrophobic, water-immiscible composition, said composition preferably having a viscosity less than 1500 mPa·sec, as determined by standard viscosity determination methods, measured at room temperature and under atmospheric pressure; and (ii) air or an aqueous solution (purified or demineralised water or a saline solution) with air. Both (i) and (ii) are preferably provided in a sealed and sterilized state, preferably in a syringe. Optionally the kit also comprises means for connecting both syringes to one another, e.g. a piece of medical tubing. The entire kit can be disposed of after preparing the foam and the treatment/examination has taken place. In the kit of parts according to the invention, the echolucent image enhancing hydrophobic, water-immiscible composition may preferably be the echolucent image enhancing hydrophobic, water-immiscible composition according to the invention.

Conveniently, the syringes may be filled with the hydrophobic, water-immiscible composition (i) and the aqueous composition (ii) in pre-determined amounts, preferably each in the range of 1-10 ml, to achieve a mixing ratio as described above. In one embodiment, the syringe (ii) contains the aqueous solution in an amount that corresponds with the maximum allowable amount to achieve a low-viscous stable foam. For instance, syringe (ii) contains an amount of aqueous solution with respect to syringe (i) containing the hydrophobic, water-immiscible composition that corresponds to a volume ratio of aqueous solution: hydrophobic, water-immiscible composition in the range of between 0:100 (i.e. no aqueous solution) and 75:25, preferably between 0:100 and 60:40, preferably between 1:99 and 50:50, more preferably between 5:95 and 40:60, most preferably between 10:90 and 25:75.

In yet another aspect, the invention pertains to a method for (medical) imaging of the fallopian tubes in a patient, said method comprising administering the above-described foamed (medical) image enhancing composition into the patient's fallopian tubes, and scanning the patient using (medical) imaging. The (medical) imaging may be part of a tubal patency test or a check on fallopian tube sterilization surgery. In a preferred embodiment, the invention pertains to the use of the foamed (medical) image enhancing composition in a patency test, i.e. to determine whether the fallopian tubes are open or closed. The composition of the invention can be applied in a control on anti-conception methods known in the art, particularly in combination with Adiana®, Essure® and OvabLoc® intratubal devices. Typically such a test is performed within 3 to 6 months after fallopian tube sterilization surgery or intratubal placement. The image enhancing composition of the invention may be used for all types of medical imaging, preferably three-dimensional ultrasound imaging, more preferably three-dimensional sonohysterography. Three-dimensional imaging requires a very stable and quiet filling of the cavity of interest, with a minimum amount of artefacts. As used herein, "image enhancement" refers to increasing the contrast of an image. The contrast enhancement may be either negative (black) or positive (white). Typically, about 1-10 ml will be enough. Constant infusion is not necessary.

Example

A syringe containing 10 ml of commercially available Lipiodol was connected to another syringe containing 5 ml demineralised water, using small plastic tubing. The water (and air) was now pumped into the other syringe, and back. This was repeated for 10 times, until a foam was produced. A single phase with milky appearance of air bubbles was obtained. Phase separation did not occur for at least 10 minutes, i.e. when monitoring was stopped.

The same experiment was repeated with 5 ml Lipiodol and 10 ml demineralised water, and the same appearance was yielded. Again, no phase separation occurred for at least 10 minutes, i.e. when monitoring was stopped.

Another experiment was done in which no water but only air was pumped injected into the Lipiodol. While there was less foaming, still a milky appearance was obtained and no phase separation occurred for at least 10 minutes, i.e. when monitoring was stopped.

The present invention has been described above with reference to a number of exemplary embodiments as shown in the drawings. Modifications and alternative implementations of some parts or elements are possible, and are included in the scope of protection as defined in the appended claims.

The invention claimed is:

1. A foamed echogenic hydrophobic, water-immiscible composition, comprising ethiodized poppyseed oil or poppyseed oil suitable for medical image enhancing in echography or sonohysterography, wherein the foam is obtainable by inserting air or gas into the hydrophobic, water-immiscible composition, and which air or gas forms bubbles which are maintained within the hydrophobic water-immiscible composition for at least 5 minutes after preparation.

2. A foamed echogenic hydrophobic, water-immiscible composition, comprising ethiodized poppyseed oil or poppyseed oil suitable for medical image enhancing in echography or sonohysterography, said composition comprising water and wherein the foam is obtainable by inserting air or gas into the hydrophobic, water-immiscible composition, and which air or gas forms bubbles which are maintained within the hydrophobic water-immiscible composition for at least 5 minutes after preparation, wherein the volume ratio of water: hydrophobic, water-immiscible composition is in the range between 1:99 and 75:25.

3. The composition according to claim 2, wherein said composition is a w/o emulsion having a volume ratio of water: hydrophobic, water-immiscible composition in the range between 1:99 and 50:50.

4. The composition according to claim 1, having a viscosity of less than 1500 mPa·s as determined by standard viscosity determination methods, measured at room temperature and under atmospheric pressure.

5. The composition according to claim 1, having a viscosity of at least 15 mPa·s as determined by standard viscosity determination methods, measured at room temperature and under atmospheric pressure.

6. The composition according to claim 1, said hydrophobic, water-immiscible composition comprising poppyseed oil or ethiodized poppyseed oil, or mixtures thereof.

7. The composition according to claim 1, said hydrophobic, water-immiscible composition comprising tocopherol equivalents.

8. The composition according to claim 1 for use in a medical imaging procedure of the fallopian tubes.

9. A method for preparing the foamed echogenic image enhancing hydrophobic, water-immiscible composition according to claim 1, by (i) providing an echolucent medical image enhancing hydrophobic, water-immiscible composition, comprising ethiodized poppyseed oil or poppyseed oil, or wherein said composition comprises safflower oil, canola oil, wheat germ, rapeseed oil, cottonseed oil and/or sunflower oil, and (ii) foaming said composition using (i) sterile air or gas; or (ii) aqueous component with sterile air or gas, to produce a foamed echogenic medical image enhancing composition.

10. A method for performing a patency test, or a check on fallopian tube sterilization surgery, said method comprising administering the composition according to claim 1 into fallopian tubes of a patient, and scanning the patient using medical imaging.

11. A method for enhancing contrast of a medical image of fallopian tubes, the method comprising introducing 1-10 ml of the medical image enhancing composition according to claim 1 into the fallopian tubes.

12. The method according to claim 11, wherein the composition is at least in part removed after echography or sonohysterography by applying a slight underpressure.

13. The composition according to claim 3, wherein said composition is a w/o emulsion having a volume ratio of water: hydrophobic, water-immiscible composition in the range between 10:90 and 25:75.

14. The method according to claim 10, wherein said surgery involves intratubal devices.

15. The composition according to claim 1, wherein said hydrophobic, water-immiscible composition comprises ethiodized poppyseed oil.

* * * * *